United States Patent [19]

Draenert

[11] 4,365,357

[45] Dec. 28, 1982

[54] SURGICAL MATERIALS SUITABLE FOR USE WITH BONE CEMENTS

[75] Inventor: Klaus Draenert, Ottobrunn, Fed. Rep. of Germany

[73] Assignee: Merck Patent Gesellschaft mit beschränkter Haftung, Darmstadt, Fed. Rep. of Germany

[21] Appl. No.: 143,570

[22] Filed: Apr. 25, 1980

[30] Foreign Application Priority Data

Apr. 28, 1979 [DE] Fed. Rep. of Germany ....... 2917446

[51] Int. Cl.³ ............................................. A61F 1/24
[52] U.S. Cl. .................................... 3/1.91; 128/92 C
[58] Field of Search ............... 128/334 R, 334 C, 335, 128/335.5, 92 R, 92 C; 3/1, 1.9, 1.91; 428/287, 903

[56] References Cited

U.S. PATENT DOCUMENTS

| | | | |
|---|---|---|---|
| 3,272,204 | 9/1966 | Artandi et al. | 128/334 R |
| 3,463,158 | 8/1969 | Schmitt et al. | 128/92 BC |
| 4,064,567 | 12/1977 | Burstein et al. | 3/1.91 |
| 4,089,071 | 5/1978 | Kalnberz | 3/1.9 |
| 4,093,576 | 6/1978 | deWjin | 260/17 R |
| 4,137,921 | 2/1979 | Okuzumi et al. | 128/335.5 |

*Primary Examiner*—Richard J. Apley
*Assistant Examiner*—T. Wallen
*Attorney, Agent, or Firm*—Millen & White

[57] ABSTRACT

A surgical network material is made from filaments of resorbable organic polymers with a thickness of about 50–300 μm and/or of non-resorbable filaments or wires with a thickness of 100–750 μm. The network which has an internal mesh width of about 1–10 mm, can be used, in particular together with bone cements based on polyacrylates or polymethacrylates, in combating bone defects.

6 Claims, No Drawings

SURGICAL MATERIALS SUITABLE FOR USE WITH BONE CEMENTS

BACKGROUND OF THE INVENTION

The present invention relates to a surgical material comprising surgical filaments which is useful in combating bone defects.

A number of materials are known for use in surgery. They can be either resorbable or non-resorbable in the body. For example, in the form of filaments or wires, they are resorbable or non-resorbable suture material, or, in the form of plates, films, pins or screws, they are used for supporting or joining parts of the skeleton. It has also already been proposed to use filament material in the form of woven, plaited or knitted textile structures to support a damaged liver, kidney or other organs. Furthermore it has been proposed to admix resorbable filaments, in the form of finely chopped pieces, into commercially available bone cements.

Commercially available bone cements of this type which are based on acrylates or methacrylates are used for filling bone defects, in so-called linking osteosyntheses, or in the implantation of endoprostheses. It is disclosed that the incorporation of resorbable filament pieces in implanted endoprostheses, after these filament pieces have been resorbed, results in pores in the non-resorbable bone cement into which body tissue can grow. It is stated that an improved long-term stability of the prosthesis is achieved in this way.

However, it is possible for endogenous tissue to grow in only those pores produced from a piece of polymer filament which happens to extend to the surface of the cement from where it can be resorbed. The filament pieces which lie inside the cement, on the other hand, cannot be reached by body fluids and resorbed. They, therefore, make no contribution to the prosthesis becoming in-grown with body tissue. Because of this, it can be expected that the long-term stability of a prosthesis which has been implanted using a bone cement to which chopped pieces of resorbable polymer filaments have been added is at best slightly improved. Since, moreover, the filament pieces incorporated must be relatively short to enable them to be mixed with the cement at all, they are also not expected to result in any improvement in the elasticity and stability of the cement socket formed around the implanted prosthesis. Specifically, in more than 60% of the cases in which femur shaft prostheses and acetabulum implants become loose, the cement socket is not able to withstand the mechanical stresses. In most cases, the cement socket is ruptured or fractured by the metal shaft or by the plastic acetabulum.

SUMMARY OF THE INVENTION

It is, therefore, an object of this invention to provide a surgical material which can be employed in the healing of bone defects, e.g., in a bone cement, and which not only improves the elasticity and stability of the cement but also guarantees the outstanding long-term stability thereof.

Upon further study of the specification and appended claims, further objects and advantages of this invention will become apparent to those skilled in the art.

These objects have been attained based on the discovery that the incorporation of an inherently coherent network of a surgical filament material of a specific filament thickness and a specific mesh width into the bone cement imparts to the bone defect treated therewith a considerably improved short-term and long-term stability.

Accordingly, this invention relates to a surgical material based on surgical filament, comprising filaments of resorbable organic polymers of a thickness of about 50–300 μm and/or non-resorbable filaments or wires of a thickness of 100–750 μm, which form a network of an internal mesh width of about 1–10 mm.

The invention also relates to the use of these materials in combating bone defects.

DETAILED DISCUSSION

The materials of this invention are advantageous in that very powerful stabilization of the bone defect is obtained even as a result of the network alone. For this purpose, it is sufficient to use only one layer of the network of this invention. As a rule, however, the material of this invention will be used in the form of several, preferably about 2–3, successive layers.

While the stabilization of the bone defect is assured immediately after introduction of the material of this invention into the body, by the cohesion of the network which is still intact, this stabilization is achieved in the end in the case of a network of resorbable organic polymers as the resorption of the organic polymers progresses, i.e., by the endogenous tissue which grows into the resulting cavities at the same time.

The dimensions of the resorbable material of this invention, i.e., a filament thickness of about 50—about 300 μm and preferably about 80—about 200 μm, and a mesh width of about 1 to about 10 mm and preferably about 2 to about 5 mm, ensure that a cavity system which has dimensions highly advantageous for bone growth forms in the non-resorbable bone cement, this system being filled by load-bearing osseous tissue at the same rate as the network is resorbed.

The stabilization of the bone defect can additionally also be affected when one layer of a multi-layer material comprises a non-resorbable material which, thus, retains its cohesion irrespective of the resorption of the other layers and thus additionally contributes to long-term stability. Examples of material which can be used for this purpose include non-resorbable organic polymer filaments, such as, for example, nylon filaments. However, it has proven particularly advantageous for one layer to consist of a network of metal filaments which are tolerated by the body and are not attacked by the body.

If desired, the entire network can also be made of a non-resorbable material, preferably of metal filaments. Although, in this case, no channels into which osseous tissue can grow are provided by resorption of filaments, very powerful stabilization of the entire implant is, however, achieved by the resistance of the non-resorbable filaments. Preferred non-resorbable filament thicknesses are about 100 to about 300 μm while preferred mesh widths are about 2 to about 5 mm.

Suitable material for the metal filaments includes, for example, titanium or an alloy of cobalt, chromium and molybdenum.

The use of at least one layer of a network of metal filaments not only provides very good stabilization but is also advantageous in that an X-ray check can be carried out on the treated bone defect very easily at any time.

All of the substances already known hitherto as resorbable surgical materials can be used per se as resorbable organic polymers for this invention. Apart from resorbability, the sole prerequisite is that these materials can be shaped to form the network of this invention. Suitable materials include not only naturally occurring materials, such as, for example, catgut or collagen, but also synthetic polymers, such as, for example, polyglycolides, polylactides or copolymers of lactide and glycolide. Polyaminoacids can also be used. These materials are known or can be prepared by known methods. It is also possible to produce filaments in any desired thickness. The joining of the filaments to produce the network of this invention is also effected in a known manner, by weaving, knitting, plaiting, interlacing, sticking or welding.

The network material of this invention can thus be produced in any desired form, e.g., to conform to the final shape of the bone cement in which it is to be disposed. For example, the metal or polymer filaments can be joined in a sheet-like shape as a nonwoven or in a shape suited to the intended application, such as tubes or cylinders or as sockets closed on one side or in the form of a sponge. For the implantation of endoprostheses in particular, the form of tubes or sockets closed on one side has very great advantages. Specifically, in the case of the implantation of a hip joint prosthesis a number of difficulties which have arisen hitherto can be overcome using the material of this invention. For example, hitherto, very great care had to be taken, e.g., by the use of special target instruments, to introduce the shaft of the prosthesis so that it was accurately centered in the femur. This prevented direct contact between the prosthesis and the bone. A further frequent occurrence was that bone cement was pressed into the medullary space when the prosthesis was introduced.

Now, using a socket made of the material of this invention, which in the simplest case can be obtained by tying off one end of a tube, this socket is first introduced into the prepared femur, for example, with the aid of the shaft of the prosthesis, and, after removing the prosthesis, is filled with the bone cement, which is still plastic and shapable. When the prosthesis is subsequently introduced, no target instrument is required since the socket of this invention centers the shaft of the prosthesis. Moreover, the resulting pressure presses the network of this invention until it meets the osseous tissue which is still intact and, at the same time, the cavities remaining between the filaments are filled with bone cement, which in this way likewise adjoins the living tissue. Pressing of bone cement into the adjoining medullary space beneath the prosthesis is very substantially prevented by the socket which is closed at the bottom. If a resorbable filament material is used, the resorbable material is then resorbed from the edge after the implantation and the resulting cavities are filled with an osseous system at the same time. Thus, as a result of the preferably multi-layer design of the material of this invention, a three-dimensional channel system forms in the non-resorbable bone cement and this system is filled with a load-bearing osseous system.

Reinforcing of the cement socket with a multi-layer metal net, which also can be constructed as a rigid metal socket in one or more layers, provides the socket with such strength that rupture of the cement socket by the shaft of the prosthesis is hardly any longer to be feared.

Incorporation of this invention's network of resorbable material in combination with one or more layers of a metal net also increases the stability of the socket formed around the prosthesis to such an extent that rupture of the cement socket by the shaft of the prosthesis or by the acetabulum prosthesis is also hardly any longer to be feared.

Of course, because of the surgical use of the network material of this invention, it is normally provided in sterile form and in a sterile package. Its dimensions are on the order of 5–30 cm, the precise dimensions being determined by the requirements of the particular use and the patient involved.

With implantation of this type, it is sometimes necessary to remove the prosthesis because of postoperative disorders. For this purpose, it has hitherto been necessary to laboriously chip out the cement socket piece by piece. It was unavoidable that considerable portions of the adjoining osseous tissue were also affected. By incorporating the network of this invention, and especially such a network which contains at least one layer of a non-resorbable, in particular metallic, network, the cement socket is, however, so stabilized that it can be removed as a whole, if necessary. Additionally, it is also possible to provide metal extraction clips on the open end of the socket for this purpose.

This stabilization of the treated bone defect is observed not only for implantations, but also when the material of this invention is put to other use, in otherwise conventional fashion, for example, in linking osteosyntheses.

Generally, the materials of this invention are processed together with one of the customary bone cements. These are generally self-polymerizing substances which are mixed immediately prior to the operation and are introduced in the plastic stage into the body, where they harden within a few minutes. Such bone cements based on acrylates or methacrylates are available commercially, for example, under the tradename Palacos ®. They are prepared by mixing about 2 parts of a finely divided prepolymer containing a polymerization catalyst (for example, dibenzoyl peroxide) with one part of a liquid monomer, which contains an accelerator (for example, dimethyl-p-toluidine), to give a shapeable mass, which is implanted in the body, where it hardens. The prepolymer used is in particular polymethyl methacrylate or a copolymer of methyl acrylate and methyl methacrylate. The monomer used is, for example, methyl acrylate or methyl methacrylate, or mixtures thereof. Particularly preferentially, the materials of this invention are processed with the implantation materials disclosed in German patent application P No. 29 05 878, corresponding to U.S. application Ser. No. 121,772, filed on Feb. 15, 1980, which are based on polyacrylates and which additionally contain about 5 to about 35% by weight of resorbable tricalcium phosphate of a particle size of 50–300 μm.

The tricalcium phosphate contained in such implantation materials on the one hand serves to stimulate osseous growth, since calcium phosphate is an essential constituent of natural bone; and on the other hand, it provides additional cavities into which the osseous tissue can grow due to resorption of the tricalcium phosphate, in this way ensuring even better toothing of the implant with its environment.

The essential advantages of the network of this invention are, however, also displayed when the material is processed with other bone cements, so that the materials of this invention can be processed with all conventional bone cements.

Thus, the network of this invention can be marketed as such to be processed with any conventional bone cement. However, preferably, the network is sold as a part of a bone cement preparation kit consisting essentially of the network shaped to a particular use, the prepolymer and the monomer. As a rule such a kit contains about 20 to about 100 g prepolymer, about 10 to about 50 ml monomer and an appropriate piece of the network of the invention.

One of the preferred kits is one for the implantation of a femur shaft prosthesis. Typically such a kit contains a cylindrical multi-layer stocking with preferably about 2-5 layers at least one of them consisting of a layer of a metal wire network, the stocking having a length of about 20 to about 30 cm, and about 40 to about 80 g of prepolymer and about 20 to about 40 ml of monomer.

Most preferred in these kits is the use of bone cements disclosed in German patent application P No. 29 05 878, corresponding to U.S. application Ser. No. 121,772, filed on Feb. 15, 1980, which additionally contain about 5 to about 35% by weight of resorbable tricalcium phosphate of a particle size of 50-300 $\mu m$ and optionally an antibiotic.

If the network materials of this invention are used without bone cement, which is the case, for example, in the treatment of fascial lacunae, tendoplasty, periosteal replacement, syndesmoplasty or bone defects, e.g., wherein the defective structures are bridged or filled by the network, they are preferably produced from polymer filaments which are provided with finely divided tricalcium phosphate incorporated therein. This incorporation of tricalcium phosphate can, for example, be effected by carrying out the plaiting of the starting material very fine polymer filaments used to prepare the required filament thickness of this invention, in the presence of tricalcium phosphate powder, in which case tricalcium phosphate particles are also plaited into the filaments produced. However, this can also be accomplished by incipiently dissolving or melting the polymer filaments on their surfaces and thus sticking the tricalcium phosphate to the surface. The resorbable polymer filaments provided with tricalcium phosphate can then be joined in a conventional manner to produce the network of this invention. A network of this type provided with tricalcium phosphate is thus also able to stimulate osseous growth in the environment.

The invention provides the surgeon with a material which can be used very advantageously both in the implantation of endoprosthesis and also in the treatment of other bone defects.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

100 meters of a surgical suture material, which is also available commercially under the name Catgut (filament thickness about 120 $\mu m$), is knitted on a circular knitting machine to an endless stocking with a mesh width of about 2 to 4 mm and a total width of 14 meshes. By drawing the stocking onto a cylinder and turning up, a two-layer stocking is obtained and by turning up twice a four-layer stocking is obtained.

EXAMPLE 2

A resorbable surgical suture material based on polylactides (filament thickness about 100 $\mu m$), which starts to melt at a temperature above 200° C., is provided at this temperature with particles of tricalcium phosphate of a particle size of 100-200 $\mu m$. Such a filament can be knitted analogously to Example 1 to give a cylindrical stocking with an internal mesh width of 2-4 mm, from which a multi-layer cylindrical stocking is obtained by turning up inwards several times. By rolling such a multi-layer cylinder into a ball, a sponge-like material is obtained which is also suitable for filling relatively large bone cavities.

EXAMPLE 3

A surgical wire material with a thickness of 150 $\mu m$ is knitted on a circular knitting machine to give a cylindrical stocking with a mesh width of 2 to 4 mm and a total width of 14 meshes. This stocking is drawn onto a hollow cylinder and pushed into a hollow cylinder of correspondingly larger circumference, onto which a stocking of resorbable material according to Example 1 has been drawn. After removing the hollow cylinders, a cylindrical, two-layer stocking is obtained in which one layer of a non-resorbable metallic network is covered by a layer of a resorbable network. By turning up this stocking inwards it is possible, for example, to obtain a four-layer stocking in which an outer, resorbable layer is followed by two non-resorbable layers and a further resorbable layer.

EXAMPLE 4

A femur shaft prosthesis is covered with a multilayer stocking produced according to Example 1 and is introduced into a medullary canal prepared for it on the proximal femur. After withdrawing the prosthesis, the stocking socket remaining in the medullary canal, the socket is filled with a conventional bone cement and the prosthesis is then carefully inserted into the stocking socket at the correct angle. During this procedure, the cement is pressed through the meshes of the stocking on all sides. The prosthesis is kept implanted under pressure until the cement has hardened, so that pressing out of the shaft by reason of the polymerization shrinkage of the plastic is prevented. After the cement has hardened, the prosthesis is implanted in a stable manner and can no longer be knocked out. When an attempt is made to remove such a prosthesis by force, a fracture of the bony socket occurs or the prosthesis is pulled out together with the cement socket, in which case the inner surface of the bone is correspondingly damaged.

A multi-layer material produced according to Example 2 or Example 3 can be used in the same way.

EXAMPLE 5

An arthrotically changed hip joint is opened, the neck of the femur is exposed and the capsule removed. The head of the hip with the neck of the femur is resected 1 cm above the trochanter minor at an angle to the horizontal plane of 40 degrees. The cotyloid cavity is freed from cartilage, the labrum acetabulare is removed and the fossa acetabuli is removed. After careful staunching of the blood, four cylindrical anchorage holes measuring 10 mm—16 mm in diameter are made in the roof of the acetabulum. A stocking produced according to Example 1 is turned up to produce several layers one on top of the other and is placed in the dried acetabular bed. The meshwork is then pressed into the anchorage holes in the roof of the acetabulum, using a surgical swab. After carefully drying out the entire bed and making a vent hole to the lateral corner of the acetabulum, which drains the depth of the anchorage holes, the bone cement is introduced and pressed firmly, with the acetabular implant, into the prepared cotyloid cavity in the correct position. Making full use of the pressure-absorbing surface in the roof of the acetabulum, the prosthesis is held immovably under pressure until the cement has hardened. After this time, the acetabular prosthesis is implanted in a stable manner and can no longer be knocked out.

EXAMPLE 6

For the treatment of a pathologic bone fracture resulting from bone metastases or bone tumors a linking osteosynthesis is carried out by introducing an 8-layer stocking cylinder, produced in accordance with Example 3, over the open ends of the fragments into the medullary space cavity in the proximal and the distal directions, so that the medullary space cavity is filled with this fabric cylinder over a distance which extends upwards and downwards from the fracture line and leaves room for at least 3–4 bone-screws for anchoring a fragment.

The meshes of this cylindrical stocking are widened somewhat at the level of the fracture line, so that the orifice of the cement syringe can be pushed through with a short plastic tube nozzle. The fabric cylinder is now filled from the inside under compression with bone cement and the screws for fixing a metal plate are fitted, either directly into the soft cement or after boring and cutting a thread in the hardened cement. An intramedullary reinforcement of the bone cement by a metal nail or by an additional metal plate is dispensed with in this way. After the cement has hardened, the screws and the metal implants have a firm hold, so that the bone can heal rapidly. Healing of the bone is not impaired by the cement plug. Along the resorbable filaments, the bone grows into the bone channels prepared in this way.

EXAMPLE 7

In certain cases, in which juxta-epiphyseal bone tumors have developed, large osseous defects, with which filling by endogenous bone can no longer be expected and because of which it is no longer ensured that the extremity has a load-bearing ability, can be linked and filled with bone cement and the extremities can be stabilized with or without metal reinforcement. For this purpose, a cylindrical stocking produced in accordance with Example 1 is shaped, by turning up over itself, to give a sponge-like network which fills the defect. The sponge-like network is now filled from the inside with bone cement, the bone cement being pressed under compression through the texture of the fabric. After the bone cement/textured fabric composite has hardened, the bones treated in this way again have a stability to load and this is a contributory factor in making care considerably easier.

A material produced in accordance with Example 2 can be used in the same way for filling relatively large bone cavities. Both the resorbable filament material and the tricalcium phosphate are resorbed by the body.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A bone cement preparation kit for bone repair or other treatment of a bone defect, consisting essentially of a surgical network material formed of physiologically acceptable filaments which are resorbable and are of a thickness of about 50—about 300 μm, the network having an internal mesh width of about 1–10 mm and having a shape appropriate to the intended use; and a prepolymer and monomer for preparation of bone cement useful in bone repair or other bone treatment.

2. The bone cement preparation kit of claim 1, having a polyacrylate or polymethacrylate base.

3. The bone cement preparation kit of claim 1, comprising a multi-layer stocking of about 20 to 30 cm length, 40 to 80 g of a polyacrylate and/or polymethacrylate, 20 to 40 ml of methylacrylate and/or methylmethacrylate, 5 to 60 g of resorbable tricalciumphosphate, and an antibiotic.

4. A method of implanting an endoprosthesis in a patient which comprises implanting the endoprosthesis using the bone cement preparation kit of claim 1.

5. A method of effecting linking osteosynthesis in a patient which comprises using the bone cement preparation kit of claim 1 to perform the linking osteosynthesis.

6. The combination of claim 1, which is of multi-layers, at least one layer being formed of filaments which are non-resorbable and are of a thickness of about 100—about 750 μm.

* * * * *

UNITED STATES PATENT AND TRADEMARK OFFICE
CERTIFICATE OF CORRECTION

PATENT NO. : 4,365,357
DATED : December 28, 1982
INVENTOR(S) : Klaus Draenert

It is certified that error appears in the above-identified patent and that said Letters Patent is hereby corrected as shown below:

Column 8, lines 49 to 52, delete claim 6.

On the Title Page, "6 Claims" should read -- 5 Claims --.

Signed and Sealed this

Sixth Day of December 1983

[SEAL]

Attest:

GERALD J. MOSSINGHOFF

Attesting Officer     Commissioner of Patents and Trademarks